United States Patent [19]

Hashimoto et al.

[11] 4,081,267
[45] Mar. 28, 1978

[54] PYRIDYLTRIAZINONE HERBICIDAL COMPOSITIONS

[75] Inventors: Shunichi Hashimoto, Takarazuka; Osamu Kirino, Ashiya; Toshiaki Ozaki, Toyonaka; Norihisa Yamashita, Takarazuka, all of Japan

[73] Assignee: Sumitomo Chemical Company, Limited, Osaka, Japan

[21] Appl. No.: 649,320

[22] Filed: Jan. 15, 1976

[30] Foreign Application Priority Data

Feb. 14, 1975  Japan .................................. 50-19041

[51] Int. Cl.² ........................................... A01N 9/22
[52] U.S. Cl. ........................................... 71/93; 544/182;
8/190; 106/138; 162/161; 252/106; 252/401;
260/45.8 NT; 424/49; 424/69; 424/249;
426/331; 426/335; 71/67; 427/397
[58] Field of Search ........................... 71/93; 424/249

[56] References Cited

U.S. PATENT DOCUMENTS

| | | |
|---|---|---|
| 3,544,570 | 12/1970 | Timmler et al. ................. 71/93 |
| 3,671,523 | 6/1972 | Westphal et al. ................ 71/93 |
| 3,855,220 | 12/1974 | Fischer .......................... 71/93 |

FOREIGN PATENT DOCUMENTS 966,283  8/1964  United Kingdom ............... 71/93

OTHER PUBLICATIONS

Takahashi et al., I" Syntheiss of 1,2,4-Triazine-5-one, etc.," (1973) J. Chem. Soc. Japan 1973 pp. 1519-1522 (1973).
Ibid II - Eng. Translation of "R" (abstract).

*Primary Examiner*—Glennon H. Hollrah
*Attorney, Agent, or Firm*—Birch, Stewart, Kolasch and Birch

[57] ABSTRACT

A herbicidal and fungicidal composition which comprises as an active ingredient a pyridyltriazinone compound of the formula:

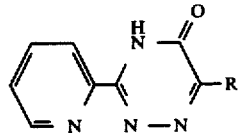

wherein R is a hydrogen atom, an alkyl group having 1 to 5 carbon atoms, an alkoxycarbonylmethyl group whose alkoxy has 1 to 3 carbon atoms or a phenyl group.

6 Claims, No Drawings

PYRIDYLTRIAZINONE HERBICIDAL COMPOSITIONS

The present invention relates to a herbicidal and fungicidal composition. More particularly, it relates to a non-medical (i.e. agricultural or industrial) composition for herbicidal and fungicidal use, and an active ingredient to be used therein and its preparation.

The active ingredient in the herbicidal and fungicidal composition of the invention is a pyridyltriazinone compound of the formula:

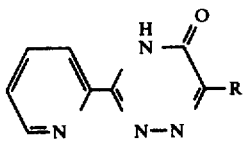
(I)

wherein R is a hydrogen atom, an alkyl group having 1 to 5 carbon atoms (e.g. methyl, ethyl, propyl, butyl, pentyl), an alkoxycarbonylmethyl group whose alkoxy has 1 to 3 carbon atoms (e.g. methoxycarbonylmethyl, ethoxycarbonylmethyl, propoxycarbonylmethyl) or a phenyl group.

Some of the pyridyltriazinone compounds (I) are per se known [cf. Nippon Kagaku Kaishi (Journal of The Chemical Society of Japan), 1973, 1519–1522]. Further, some 1,2,4-triazin-5-one derivatives are known to show a herbicidal activity [cf. Japanese patent publication Nos. 315/1969 and 20106/1970]. However, studies on the biological activity of the pyridyltriazinone compounds (I) has never been attempted.

It has now been found the pyridyltriazinone compounds (I) exhibit excellent herbicidal and fungicidal activities. It may be noted that their herbicidal activity is much stronger than the known 1,2,4-triazinon-5-one derivatives. It may be also noted that their fungicidal activity is effective against a wide variety of photopathogenic fungi. It may be further noted that they exert a notable antimicrobial activity against various fungi and bacteria parasitic on industrial articles and products. Advantageously, the toxicity of the pyridyltriazinone compounds (I) to mammals and fishes is remarkably low.

Some specific examples of the pyridyltriazinone compounds (I) are shown in the following table:

Table 1

| Compound No. | Chemical structure | Physical constant |
|---|---|---|
| 1 | 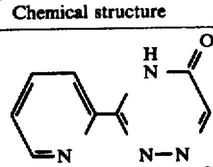 | M.P. 217–219° C (decomp.) |
| 2 | 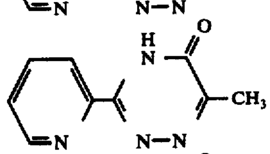 | M.P. 299–300° C |
| 3 | 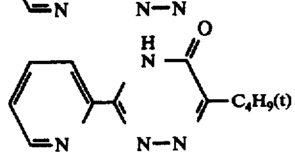 | M.P. 114–115° C |

Table 1-continued

| Compound No. | Chemical structure | Physical constant |
|---|---|---|
| 4 | 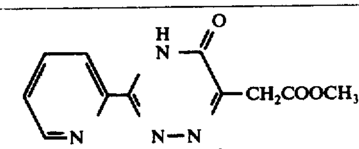 | M.P. 124–126° C |
| 5 | 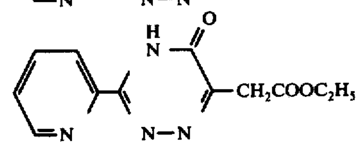 | M.P. 136–137° C |
| 6 | 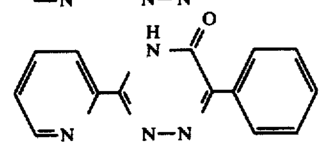 | M.P. 177–178° C |

The pyridyltriazinone compounds (I) may be produced by various methods, of which some typical examples are shown below.

The pyridyltriazinone compound (I) can be produced by reacting picoline amidrazone of the formula:

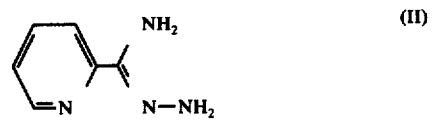
(II)

with a haloacetic acid or its ester of the formula:

(III)

wherein X is a halogen atom (e.g. chlorine, bromine, iodine), R' is a hydrogen or an alkyl group having 1 to 3 carbon atoms (e.g. methyl, ethyl, propyl) and R is as defined above and oxidizing the resultant product of the formula:

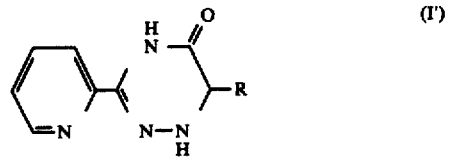
(I')

wherein R is as defined above.

The reaction in the first step may be carried out in an inert solvent (e.g. benzene, chlorobenzene, toluene, xylene, ligroin, hexane, isopropyl ether, tetrahydrofuran, dioxane, chloroform, methanol, ethanol, isopropanol, water), preferably in the presence of an acid-eliminating agent (e.g. sodium hydroxide, potassium hydroxide, sodium methoxide, sodium ethoxide, pyridine, triethylamine, dimethylaniline, diethylaniline) at a wide range of temperature from cooling to heating. The oxidation in the second step may be effected in an inert solvent (e.g. methanol, ethanol, isopropyl ether, tetrahydrofuran, dioxane, acetone, chloroform) under light irradiation or with an oxidizing agent (e.g. chromic acid, perchromic acid, potassium permanganate, manganese dioxide, aqueous hydrogen peroxide, perbenzoic acid).

In an alternative procedure, the pyridyltriazinone compound (I) may be produced by reacting the picoline amidrazone (II) with a keto-acid or its ester of the formula:

$$R-CO-COOR' \qquad (IV)$$

wherein R and R' are each as defined above. The reaction may be carried out in an inert solvent (e.g. water, methanol, ethanol, isopropyl ether, tetrahydrofuran, dioxane, acetone, chloroform) at a wide range of temperature from cooling to heating.

Still, the pyridyltriazinone compound (I) wherein R is alkoxycarbonylmethyl may be produced by another alternative procedure, i.e. reacting the picoline amidrazone (II) with an acetylenedicarboxylic acid ester of the formula:

$$R''OOC-C \equiv C-COOR'' \qquad (V)$$

wherein R'' is an alkyl group having 1 to 3 carbon atoms (e.g. methyl, ethyl, propyl). The reaction may be carried out in an inert solvent (e.g. methanol, ethanol, isopropyl ether, tetrahydrofuran, dioxane, acetone, chloroform) at a wide range of temperature from cooling to heating.

The thus produced pyridyltriazinone compounds (I) may be recovered from the reaction mixture by a conventional separation procedure, optionally followed by purification.

Some specific examples of the process for preparation of the pyridyltriazinone compounds (I) are as follows:

EXAMPLE 1

In a 200 ml four-necked flask were charged 13.6 g of picoline amidrazone, 15 g of triethylamine and 100 ml of benzene, and the mixture was cooled below 10° C while stirring. After the dropwise addition of 18.4 g of ethyl bromoacetate at 10° to 15° C while stirring, the resulting mixture was heated under reflux for 2 hours. The reaction mixture was cooled, and the deposited triethylamine hydrobromide was removed by filtration. Removal of the solvent under reduced pressure gave 12.9 g of 3-(2-pyridyl)-1,4,5,6-tetrahydro-1,2,4-triazin-5-one as white crystals. M.P. 138°–139° C. Anal. Calcd. for $C_8H_8N_4O$: C, 54.55%; H, 4.55%; N, 31.82%. Found: C, 54.38%; H, 4.63%, N, 32.01%.

In a 500 ml four-necked flask was charged a solution of 7.4 g of the above prepared 3-(2-pyridyl)-6-methyl-1,4,5,6-tetrahydro-1,2,4-triazin-5-one in 200 ml of acetone, and a solution of 3.2 g of potassium permanganate in 200 ml of acetone was added dropwise thereto at 10° to 15° C while stirring. The resulting mixture was stirred for 2 hours, and then the produced manganese dioxide was removed by filtration. The acetone was removed under reduced pressure to obtain 6.5 g of 3-(2-pyridyl)-6-methyl-4,5-dihydro-1,2,4-triazin-5-one as white crystals. M.P. 299°–300° C. Anal. Calcd. for $C_9H_8N_4O$: C, 57.45%; H, 4.26%; N, 29.79%. Found: C, 57.31%; H, 4.22%; N, 29.95%.

EXAMPLE 2

In a 100 ml four-necked flask were charged 6.8 g of picoline amidrazone and 40 ml of water, and 6.5 g of trimethylpyruvic acid were dropwise added thereto at 10° to 15° C while stirring. The resulting mixture was heated at 60° C for 1 hour. The reaction mixture was cooled, and the deposited white crystals were collected by filtration to obtain 8.7 g of 3-(2-pyridyl)-6-tert.-butyl-4,5-dihydro-1,2,4-triazin-5-one. M.P. 114°–115° C. Anal. Calcd. for $C_{12}H_{14}N_4O$: C, 62.61%; H, 6.09%; N, 24.35%. Found: C, 62.56%; H, 5.87%; N, 24.37%.

EXAMPLE 3

In a 100 ml four-necked flask were charged 6.8 g of picoline amidrazone and 40 ml of ethanol, and 8.5 g of diethyl acetylenedicarboxylate were dropwise added thereto at 10° to 15° C while stirring. The resulting mixture was heated under reflux for 3 hours. The solvent was removed under reduced pressure to obtain 12.4 g of 3-(2-pyridyl)-6-ethoxycarbonylmethyl-4,5-dihydro-1,2,4-triazin-5-one. M.P. 136°–137° C. Anal. Calcd. for $C_{12}H_{12}N_4O_3$: C, 55.38%; H, 4.62%; N, 21.54%. Found: C, 55.21%; H, 4.54%; N, 21.71%.

Other pyridyltriazinone compounds (I) may be prepared in the same procedure as above.

The pyridyltriazinone compounds (I) show a strong herbicidal activity on grassy weeds such as barnyard grass (*Echinochloa crus-galli*) and large crabgrass (*Digitaria sanguinalis*), and weeds in upland and paddy fields such as nutsedge sp. (*Cyperus difformis*), redroot pigweed (*Amaranthus retroflexus*), common lambsquarter (*Chenopodium album*), chickweed (*Stellaria media*) and toothcup (*Rotala indica* Koehne). They exert their herbicidal effect on foliage treatment and also on pre-emergence treatment. Their selectivity is so remarkable that any appreciable harmful effect is not seen on many crops such as rice plant, wheat, radish, soybean, cotton, beet, corn and rapeseed. Therefore, the pyridyltriazinone compounds (I) are useful as herbicides for fields, paddy rice fields, orchards, turfs, pasture lands, woods and forests, non-crop lands, etc.

When the pyridyltriazinone compounds (I) are used as herbicides, they may be applied as such or in any of the preparation forms such as dusts, granules, fine granules, wettable powders and emulsifiable concentrates. These preparations can be produced in combination with solid carriers and liquid carriers. The solid carriers include, for example, talc, bentonite, clay, kaolin, diatomaceous earth, vermiculite, slaked lime, etc., and the liquid carriers include, for example, benzene, alcohols, acetone, xylene, methylnaphthalene, dioxane, cyclohexanone, etc. In the practical application, they may be applied in combination with surfactants for agricultural use, for example, spreaders in order to promote and ensure the herbicidal activity, or may be applied in combination with agricultural chemicals such as fungicides, insecticides and fertilizers. They may be also used together with any other herbicides.

In general, the pyridyltriazinone compounds (I) may be contained in the compositions for herbicidal use at a concentration of from 0.1 to 95% by weight.

Very often, the pyridyltriazinone compounds (I) are formulated as concentrated compositions which are applied either to the soil or the foliage in the form of water dispersions or emulsions containing the same in the range of from 0.1 to 5% by weight. Water-dispersible or emulsifiable compositions are either solids usually known as wettable powders, or liquids usually known as emulsifiable concentrates. These concentrated compositions may be used in the range:

|  | % by weight |
| --- | --- |
| Pyridyltriazinone compound (I) | 10 – 80 |
| Surfactant | 3 – 10 |
| Inert carrier | 87 – 10 |

Wettable powders comprise an intimate, finely-divided mixture of the pyridyltriazinone compounds (I), an inert carrier and surfactants. The concentration of the compound is usually from 10 to 90% by weight. The inert carrier is usually chosen from among attapulgite clays, kaolin clays, montmorillonite clays, diatomaceous earths and purified silicates. Effective surfactants, comprising from 0.5 to 10% by weight of the wettable powder, are found among sulfonated lignins, condensed naphthalenesulfonates, naphthalenesulfonates, alkylbenzenesulfonates, alkyl sulfates and nonionic surfactants such as ethylene oxide adducts of phenol.

Typical emulsifiable concentrates of the pyridyltriazinone compounds (I) comprise a convenient concentration of the same, such as from about 100 to 500 g per liter of liquid, dissolved in an inert carrier which is a mixture of a water-immiscible solvent and emulsifiers. Useful organic solvents include aromatics, especially xylenes, and petroleum fractions, especially the high-boiling naphthalenic and olefinic portions of petroleum. Many other organic solvents may also be used such as terpenic solvents, and complex alcohols such as 2-ethoxyethanol. Suitable emulsifiers for emulsifiable concentrates are chosen from the same types of surfactants used for wettable powders.

When the pyridyltriazinone compounds (I) are to be applied to the soil, as for a pre-emergence application, it is convenient to use a granular formation. Such a formulation typically comprises the compound dispersed on a granular inert carrier such as coarsely ground clay. The particle size of the granules usually ranges from about 0.1 to 3 mm. The usual formulation process for granules comprises dissolving the compound in an inexpensive solvent and applying the solution to the carrier in an appropriate solid mixer. Granular compositions are usually in the following range:

|  | % by weight |
| --- | --- |
| Pyridyltriazinone compound (I) | 1 – 10 |
| Surfactant | 0 – 2 |
| Inert carrier | 99 – 88 |

Somewhat less economically, the pyridyltriazinone compounds (I) may be dispersed in a dough composed of damp clay or any other inert carrier, and the resulting dispersion is then dried and coarsely ground to produce the desired granular product.

The best application rate of the pyridyltriazinone compounds (I) for the control of a given weed varies, of course, depending upon the method of compound application, climate, soil type, water and organic matter contents of the soil and other factors known to those skilled in plant science. It will be found, however, that the optimum application rate is in the range of from 0.25 to 300 g/are in virtually every case. The optimum rates will usually be found to be within the preferred range of from 0.25 to 100 g/are.

The time when the pyridyltriazinone compounds (I) should be applied to the soil or the weeds is widely variable, since they are effective at both pre-emergence and post-emergence. At least some control of weeds will result from application of the compounds at any time when weeds are growing or germinating. They may also be applied to the soil during a dormant season to kill weeds germinating during the following warm season.

When the pyridyltriazinone compounds (I) are used for weed control in an annual crop, it is usually best to apply a pre-emergence application of the compound to the soil at the time the crop is being planted. If the compound is to be soil incorporated, it will usually be applied and incorporated immediately before planting. If it is to be surface applied, it is usually simplest to apply the compound immediately after planting.

The following Examples show some specific examples of the composition suitable for herbicidal use, in which parts(s) and % are by weight, and the numbers of the compounds used as the active ingredient correspond to those in Table 1:

EXAMPLE A

Wettable powder:

Twentyfive parts of Compound No. 2, 5 parts of a surfactant (i.e. polyoxyethylene alkylaryl ether) and 70 parts of talc are pulverized and mixed well to make a wettable powder preparation containing the active ingredient in 25% concentration.

EXAMPLE B

Emulsifiable concentrate:

Thirty parts of Compound No. 5, 20 parts of a surfactant (i.e. polyethylene glycol ether) and 50 parts of cyclohexanone are mixed well to make an emulsifiable concentrate preparation containing the active ingredient in 30% concentration.

EXAMPLE C

Granules:

Five parts of Compound No. 1, 40 parts of bentonite, 50 parts of clay and 5 parts of sodium lignosulfonate are pulverized and mixed well. The resulting mixture is kneaded well with water, granulated and dried to obtain a granular preparation containing the active ingredient in 5% concentration.

EXAMPLE D

Granules:

Three parts of Compound No. 1, and 97 parts of clay are pulverized and mixed well to make a granular preparation containing the active ingredient in 3% concentration.

EXAMPLE E

Fine granules:

Five parts of Compound No. 3, 4 parts of sodium lignosulfonate, 86 parts of clay ("Fubasami clay", trademark of Fubasami Clay Co., Ltd.) and 5 parts by weight of water are kneaded by means of a ribbon mixer and dried to obtain a fine granular preparation containing the active ingredient in 5% concentration.

The pyridyltriazinone compounds (I) can control plant diseases and are particularly effective in controlling or exterminating plant diseases such as stem rot of vegetables (*Sclerotinia* spp.) and gray mold of vegetables (*Botrytis* spp.). Furthermore, they have a strong protective activity against plant pathogens such as rice blast (*Pyricularia oryzae*), sheath blight of rice (*Pellicu-*

*laria sasakii*), helminthosporium leaf spot of rice (*Cochliobolus miyabeanus*), bacterial leaf blight of rice (*Xanthomonas oryzae*), brown rot of peach (*Sclerotinia cinerea*), blossom blight of apple (*Sclerotinia mali*), damping off yellows of Japanese radish (*Fusarium oxysporum f. raphani*), southern blight of kidney bean (*Corticium rolifsii*), powdery mildew of cucumber (*Sphaerotheca fuliginea*), anthracnose of cucumber (*Collectotrichum spp.*), late blight of tomato (*Phytophthora infestans*), black spot of pear (*Alternaria kikuchiana*), alternaria leaf spot of apple (*Alternaria mali*), ripe rot of grape (*Glomerella cingulata*), early blight of tomato (*Alternaria solani*) and bacterial canker of citrus (*Xanthomonus citri*). Accordingly, they are useful as fungicides in agriculture.

The pyridyltriazinone compounds (I) also exhibit a strong antimicrobial activity on other microorganisms than the plant pathogens as described above. Thus, they can be used in combination with various industrial articles or products such as synthetic resins, paints, paper and fiber products for protection from bacterial or fungal infestation or damage. Further, they can be used as antimicrobial additives, washing agents, antiseptic agents and the like. Moreover, they can control or exterminate slimes, algae and other injurious organisms which attach to various bodies in the sea and do damage thereto, so that they may be applied, in various preparation forms, to water for industry, cooling and papermaking, thus controlling the slimes, algae and the like which generate in the water.

Advantageously, the pyridyltriazinone compounds (I) are very low in toxicity to mammals and fishes and hardly irritate the skin even at the actual concentration in use. Thus, they have a very high safety and practicality.

For exterminating algae and microorganisms or for controlling injurious life in water, they may be used in any of the common preparation forms such as dusts, wettable powders, oil sprays, aerosols, tablets, emulsifiable concentrates, granules, fine granules and fumigants. In general, the preferred content of the active ingredient(s) (optionally including other active components) in the preparation is from 0.1 to 95.0% by weight, preferably from 0.2 to 90.0% by weight, and the preferred amount of the active ingredient(s) used is usually from 1 to 3,000 g/10 are, preferably from 10 to 2,000 g/10 are. In the field application, the active ingredient(s) are generally used in a concentration of 1.0 to 0.01% by weight according to the object of application. The amount and concentration used depend upon the preparation forms, application time, application methods, places and objects for application and the like so that they may be changed freely irrespective of the ranges described above. The above-mentioned preparations can be used effectively by any of the application methods, for example, dusting (scattering of dusts), spraying, scattering of granules, soil-treatments, dressing, coating, dipping and the like.

The pyridyltriazinone compounds (I) can also be applied by the ultra-low volume spraying method, for example, in such a high concentration as 95% by weight of the active ingredient or even 100% by weight of the active ingredient. In the case of granules, the particle size is made uniform in the vicinity of 250 mesh, and they are applied according to the object of the application.

Furthermore, the pyridyltriazinone compounds (I) can be applied in combination with other chemicals such as Blasticidin-S, Kasugamycin, Polyoxin, Validamycin, Cellocidin, 3-[2-(3,5-dimethyl-2-oxocyclohexyl)-2-hydroxyethyl]-glutarimide, streptomycin, griseofluvin, pentachloronitrobenzene, pentachlorophenol, hexachlorobenzene, trichloronitromethane, 1,1,1-trichloro-2-nitroethane, dichlorodinitromethane, trichloronitroethylene, 1,1,2,2,-tetrachloronitroethane, methylene-bis-thiocyanate, 2,6-dichloro-4-nitroaniline, zinc ethylene-bis-dithiocarbamate, zinc dimethyldithiocarbamate, manganous ethylene-bis-dithiocarbamate, bis(dimethylthiocarbamoyl)disulfide, 2,4,5,6-tetrachloroisophthalonitrile, 2,3-dichloro-1,4-naphthoquinone, tetrachloro-p-benzoquinone, p-dimethylaminobenzene diazo sodium sulfonate, 2-(1-methylheptyl)-4,6-dinitrophenyl crotonate, 2-heptadecylimidazoline acetate, 2,4-dichloro-6-(o-chloroanilino)-S-triazine, dodecylguanidine acetate, 6-methyl-2,3-quinoxalinedithiol cyclic-S,S-dithiocarbonate, 2,3-quinoxalinedithiol cyclic trithiocarbonate, N-trichloromethylthio-4-cyclohexene-1,2-dicarboxyimide, N-(1,1,2,2-tetrachloroethylthio)-4-cyclohexene-1,2-dicarboxyimide, N-(dichlorofluoromethylthio)-N-(dimethylsulfamoyl)-aniline, 1,2-bis-(3-methoxycarbonyl-2-thioureido)benzene, 1,2-bis-(3-ethoxycarbonyl-2-thioureido)benzene, 2-amino-1,3,4-thiadiazole, 2-amino-5-mercapto-1,3,4-thiadiazole, O-phenylphenol, N-(3,5-dichlorophenyl)maleimide, N-(3,5-dichlorophenyl)succinimide, N-(3,5-dichlorophenyl)itaconimide, 3-(3,5-dichlorophenyl)-5,5-dimethyloxazolidine-2,4-dione, 2,3-dihydro-5-carboxanilide-6-methyl-1,4-oxathiine-4,4-dioxide, 2,3-dihydro-5-carboxanilide-6-methyl-1,4-oxathiine, 1-(N-n-butylcarbamoyl)-2-methoxycarbonylaminobenzimidazole, O,O-diisopropyl-S-benzyl-phosphorothioate, O-ethyl-S,S-diphenylphosphorodithioate, O-butyl-S-benzyl-S-ethylphosphorodithioate, O-ethyl-O-phenyl-O-(2,4,5-trichlorophenyl)phosphate, O,O-dimethyl-O-(3-methyl-4-nitrophenyl)-phosphorothioate, S-[1,2-bis-(ethoxycarbonyl)ethyl]-O,O-dimethylphosphorodithioate, O,O-dimethyl-S-(N-methylcarbamoylmethyl)phosphorodithioate, O,O-diethyl-O-(2-isopropyl-6-methyl-4-pyrimidyl)thiophosphate, 3,4-dimethylphenyl-N-methylcarbamate, iron methanearsonate, ammonium iron methanearsonate, 2-chloro-4,6-bis-(ethylamino)-S-triazine, 2,4-dichlorophenoxyacetic acid (including salts and esters thereof), 2-methyl-4-chlorophenoxyacetic acid (including salts and esters thereof), 2,4-dichlorophenyl-4'-nitrophenyl ether, sodium pentachlorophenolate, N-(3,4-dichlorophenyl)-propionamide, 3-(3,4-dichlorophenyl)-1,1-dimethylurea, α,α,α-trifluoro-2,6-dinitro-N,N-di-n-propyl-p-toluidine, 2-chloro-2',6'-diethyl-N-(methoxymethyl)acetamide, 1-naphthyl-N-methylcarbamate, methyl-N-(3,4-dichlorophenyl)carbamate, 4-chlorobenzyl-N,N-dimethylthiolcarbamate, N,N-diallyl-2-chloroacetamide, O-ethyl-O-(3-methyl-6-nitrophenyl)-N-sec.-butylphosphorothioamidate, S-n-butyl-S'-(p-tert.-butylbenzyl)-N-(3-pyridyl)imidodithiocarbonate and S-n-heptyl-S'-(p-tert.-butylbenzyl)-N-(3-pyridyl)imidodithiocarbonate.

In these cases, the individual active ingredient in the mixed preparation does not show a reduction in its own controlling effect, so that it is possible to control two or more kinds of injurious organisms at the same time. Further, a synergistic effect due to mixing which is expected to be sufficiently effective is observed with some combinations.

The pyridyltriazinone compounds (I) can also be used in combination with other agricultural chemicals such as fungicides, nematocides and acaricides and/or fertilizers.

For an industrial use, the pyridyltriazinone compounds (I) can be applied in the pure form without adding other inert components. They are soluble in most solvents so that the compounds may be formulated into a suitable preparation form such as a solution, together with other inert components (various carriers), and applied by mixing with industrial products or by coating, injection, dipping or the like as the need arises.

When the pyridyltriazinone compounds (I) are used for industrial purposes, they can directly be incorporated in the materials to be protected, for example, fiber products (particularly blended materials of cellulose or viscose), materials containing synthetic resin substrates such as polyamide or polyvinylchloride, casein-containing paints or lacquers, inorganic or organic pigments, thickening agents made from starch or cellulose derivatives, animal viscous materials or oils, permanent dressings containing polyvinyl alcohol as a substrate, cosmetics such as a soap or cream, ointments, powders, toothpowders and the like. Further, the compounds of this invention can be used in the form of an aerosol, dry cleaner, organic solution for use as a impregnant for wood, and emulsified solution.

Still further, the pyridyltriazinone compounds (I) can be used for protecting substances which are easy to rot, for example, leather, paper and the like in the form of an aqueous suspension together with a wetting agent or dispersing agent.

The preferred application of the pyridyltriazinone compounds (I) is disinfection of washed products and protection of the products from attack of microorganisms. For this purpose, it is preferred to use the pyridyltriazinone compounds (I) in the form of a washing liquor containing them in 0.1 to 500 ppm concentration. But the concentration is not always limited to this range.

The pyridyltriazinone compounds (I) are soluble in most organic solvents, irrespective of a hydrophilic solvent or a solvent which is immiscible with water, for example, benzene, xylene, ether, dioxane, acetone, methyl isobutyl ketone, cyclohexanone, isophorone, chloroform, trichloroethane, methylcellosolve, ethylcellosolve, butylcellosolve, dimethylformamide, dimethylsulfoxide, acetonitrile, methylnaphthalene and the like.

The pyridyltriazinone compounds (I) of this invention may be used, rather preferably, in combination with the following fungicides which have conventionally been used for industrial purposes, and in this case the controlling effect of the component active ingredients is not reduced due to the combination but rather a synergistic effect due to the combination is sufficiently expected: halogenated phenols such as pentachlorophenol, 2,4,5-trichlorophenol, 2,4,6-trichlorophenol and salts thereof, copper compounds such as cuprous oxide, cupric oxide and copper naphthenate, tin compounds such as bis(tributyltin)oxide, bis(tributyltin)chloride, bis(tributyltin)acetate and bis(tributyltin)hydroxide (in this case, the tributyl group may be replaced by a trialkyl or triphenyl group), aminobenzoic esters such as butyl p-aminobenzoate, salicylic acid derivatives such as salicylanilide and halogenated salicylanilide, chlorohexidine, monoalkyl-bis(aminoethyl)glycine and salts thereof, 1,2-benzisothiazolin-3-one, benzyl bromoacetate, 2-(4-thiazolyl)benzimidazole, p-chloro-m-xylenol, 2,2'-dihydroxy-5,5'-dichlorophenylmethane, dehydroacetic acid, formalin, nitrofurans, oxyquinolines, o-phenylphenol, biphenyl, cresol soap, creosote, dimethyl zinc, dithiocarbamates, benzothiazoles, methylene-bis-thiocyanate, etc.

The following examples show some specific examples of the composition suitable for fungicidal use, in which part(s) and % are by weight, and the numbers of the compounds used as the active ingredient correspond to those in Table 1:

EXAMPLE O

Wettable powder:

Fifty parts of Compound No. 1, 5 parts of a wetting agent (i.e. alkylbenzenesulfonate) and 45 parts of diatomaceous earth are pulverized and mixed well to make a wettable powder preparation containing the active ingredient in 50% concentration.

EXAMPLE P

Dust:

Seven parts of Compound No. 2 and 93 parts of clay are pulverized and mixed well to make a dust preparation containing the active ingredient in 7% concentration.

EXAMPLE Q

Pellets:

Eight parts of Compound No. 3, 35 parts of bentonite, 52 parts of clay and 5 parts of sodium ligninsulfonate are pulverized and mixed well. The mixture is kneaded with water and pelletized to make a pellet preparation containing the active ingredient in 8% concentration.

EXAMPLE R

Emulsifiable concentrate:

Twenty parts of Compound No. 4, 15 parts of an emulsifier (i.e. polyoxyethyleneglycol ether) and 65 parts of cyclohexanol are mixed well to make an emulsifiable concentrate preparation containing the active ingredient in 20% concentration.

EXAMPLE S

Granules:

Five parts of Compound No. 6, 93.5 parts of clay and a binder (i.e. polyvinyl alcohol) are sufficiently pulverized and mixed together. The resulting mixture is kneaded with water, granulated and dried to obtain a granular preparation containing the active ingredient in 5% concentration.

Some of the test results which support the herbicidal and fungicidal effects of the pyridyltriazinone compounds (I) are shown in the following Examples wherein part(s) are by weight. In these Examples the numbers of the compounds according to this invention correspond to those as shown in Table 1, while the numbers of the known compounds for comparison correspond to those as shown in the following table:

Table 2

| Compound No. | Chemical structure | Literature |
|---|---|---|
| i | $CH_3$, $CH_3S$- structure with N—N | Japanese Pat. Publication No. 20106/1970 |

Table 2-continued

| Compound No. | Chemical structure | Literature |
|---|---|---|
| ii | CH₃S—C(=N-N=C(CH₃)(N)—C(=O)—CH₂CH₂COOCH₃) | Japanese Pat. Publication No. 20106/1970 |
| iii | CH₃S—C(=N-N=C(CH₃)(N)—C(=O)—CH₃) | Japanese Pat. Publication No. 20106/1970 |
| iv | N=CH-pyridyl, CH₃S—C(=N-N=C)—C(=O)—phenyl | Japanese Pat. Publication No. 315/1969 |
| v | CH₃S—C(=N-N=C(C₂H₅)(N))—C(=O)—phenyl | Japanese Pat. Publication No. 20106/1970 |
| vi | CH₂=CHCH₂S—C(=N-N=C(CH₃)(N))—C(=O)—phenyl | Japanese Pat. Publication No. 20106/1970 |

EXAMPLE I

Pre-emergence application:

Taking large crabgrass (*Digitaria sanguinalis*) as a representative of grassy weeds, redroot pigweed (*Amaranthus retroflexus*) and common lambsquarter (*Chenopodium album*) as representatives of broad-leaved weeds and wheat and radish as representatives of crops, seeds of the grasses and crops were each sowed in a 10 cm flower pot and covered with soil. Each emulsifiable concentrate containing the test compound was diluted with water and applied to the soil treatment by means of a hand sprayer. Each of the grasses and crops was grown up in a green-house, and the herbicidal activity of the test compound was checked 20 days after the application. The herbicidal activity was evaluated by the following numerals ranging from 0 to 5 as follows:

| Numeral | Percentage of inhibition (%) |
|---|---|
| 0 | 0 |
| 1 | 20 |
| 2 | 40 |
| 3 | 60 |
| 4 | 80 |
| 5 | 100 |

The results are shown in Table 3.

Table 3

| Compound No. | Amount applied (g/a) | Large crab-grass | Radish | Redroot pigweed | Wheat |
|---|---|---|---|---|---|
| 1 | 20 | 5 | 1 | 5 | 0 |
|   | 10 | 5 | 0 | 5 | 0 |
| 2 | 20 | 5 | 2 | 5 | 0 |
|   | 10 | 5 | 0 | 5 | 0 |
| 3 | 20 | 5 | 0 | 5 | 0 |
|   | 10 | 4 | 0 | 3 | 0 |
| 4 | 20 | 5 | 0 | 5 | 0 |
|   | 10 | 3 | 0 | 3 | 0 |
| 5 | 20 | 5 | 0 | 5 | 0 |
|   | 10 | 4 | 0 | 3 | 0 |
| 6 | 100 | 5 | 0 | 5 | 0 |
|   | 50 | 5 | 0 | 5 | 0 |
| i | 20 | 4 | 4 | 4 | 4 |
|   | 10 | 3 | 4 | 2 | 4 |
| v | 20 | 4 | 4 | 4 | 1 |
|   | 10 | 3 | 3 | 2 | 0 |
| vi | 20 | 4 | 4 | 3 | 4 |
|   | 10 | 2 | 4 | 2 | 3 |

EXAMPLE II

Flood-water application:

A Wagner pot of 14 cm in diameter was filled with 1.5 kg of paddy field soil and thereby brought into the state of a paddy field. In the pot were transplanted rice seedlings of 3-leaf stage and further were sowed seeds of barnyard grass (*Echinochloa crus-galli*). A required amount of the test compound was applied to the soil under water-logged condition. Twenty-five days after the application, the herbicidal activity and phytotoxicity of the test compound were checked on the transplanted and sowed plants and spontaneously germinated broadleaved weeds such as monochoria (*Monochoria viaginalis* Presl.), false pimpernel (*Linderna pyxidaria*) and toothcup (*Rotala indica* Koehne).

As for the application, wettable powder containing a pre-determined amount of the test compound was applied in a proportion of 15 ml/pot by means of a pipette. The herbicidal activity was evaluated by the following numerals ranging from 0 to 5.

| Numerals | Percentage of (%) |
|---|---|
| 0 | 0 |
| 1 | 20 |
| 2 | 40 |
| 3 | 60 |
| 4 | 80 |
| 5 | 100 |

As for the evaluation of phytotoxicity, the three factors (i.e. height of grass, number of tillers and total weight (dry weight)) were each checked, and a ratio of the treated plot to the untreated plot was calculated for each factor. The phytotoxicity was evaluated based on the lowest value of the three ratios which was classified into the following grades ranging from 0 to 5.

| Grade | Ratio of the untreated plot (%) |
|---|---|
| 0 | 100 |
| 1 | 80 |
| 2 | 60 |
| 3 | 40 |
| 4 | 20 |
| 5 | 0 |

The results are shown in Table 4.

Table 4

| Compound No. | Amount applied (g/a) | Herbicidal activity Barnyard grass | Broad-grass | Phyto-toxicity (Wheat) |
|---|---|---|---|---|
| 1 | 20 | 5 | 5 | 1 |
|   | 10 | 5 | 5 | 0 |
| 2 | 20 | 5 | 5 | 1 |
|   | 10 | 5 | 5 | 0 |
| 3 | 20 | 5 | 4 | 1 |
|   | 10 | 4 | 4 | 0 |
| 4 | 20 | 5 | 4 | 1 |
|   | 10 | 3 | 4 | 0 |
| 5 | 20 | 5 | 4 | 1 |
|   | 10 | 4 | 4 | 0 |
| 6 | 100 | 5 | 5 | 0 |
|   | 50 | 5 | 5 | 0 |
| i | 20 | 3 | 2 | 2 |
|   | 10 | 2 | 1 | 1 |
| v | 20 | 3 | 3 | 3 |
|   | 10 | 1 | 2 | 2 |
| vi | 20 | 3 | 3 | 2 |
|   | 10 | 3 | 2 | 1 |

EXAMPLE III

Protective activity on rice blast (*Pyricularia oryzae*):

Rice plants (var.: Wase-Asahi) were grown up to a 3-leaf stage in a 10 cm flower pot. Each solution containing a pre-determined amount of the test compound was sprayed on the rice plants in a proportion of 7 ml/pot. After one day, a spore suspension of *Pyricularia orysae* was inoculated by spraying, and the fungicidal activity of the test compound was checked. The percentage of control was calculated from the following equation:

$$\text{Percentage of control (\%)} = \frac{\left(\begin{array}{c}\text{Number of spots}\\ \text{in the un-}\\ \text{treated plot}\end{array}\right) - \left(\begin{array}{c}\text{Number of spots}\\ \text{in the treated}\\ \text{plot}\end{array}\right)}{\text{Number of spots in the untreated plot}} \times 100$$

The results are shown in Table 5.

Table 5

| Compound No. | Concentration of active ingredient (ppm) | Percentage of control | Phyto-toxicity |
|---|---|---|---|
| 1 | 100 | 100.0 | None |
| 2 | 100 | 98.8 | " |
| 3 | 100 | 99.2 | " |
| 4 | 100 | 96.4 | " |
| 5 | 100 | 97.5 | " |
| 6 | 100 | 92.6 | " |
| i | 100 | 5.4 | " |
| Untreated plot | — | 0 | — |

EXAMPLE IV

Use in washing liquor:

One part of the test compound (i.e. Compound No. 1, 2 or 5) was dissolved in 20 parts of dimethylsulfoxide, and the resulting solution was added to a washing liquor containing a sodium soap of 1.5 g per liter so as to make a concentration of 25 mg of the test compound per liter. White cotton fabric (1 part) was dipped in the resulting liquor (20 parts), and the bath was heated at 80° C. The fabric material was treated at the same temperature for 20 minutes and rinsed at first for 40 minutes and next for 3 minutes with soft water. Thereafter the fabric material was dehydrated by a centrifuge, dried and ironed. The finished fabric material was cut into round test pieces of 20 mm in diameter. The test pieces were placed on the agar medium in a Petri dish inoculated with either *Staphylococcus aureus* 209P or *Escherichia coli* K-12 and incubated for 24 hours, and incubation was carried out at 37° C for 24 hours. After the incubation, it was found that the microorganisms did not live on the test pieces treated with each of Compound Nos. 1, 2 and 5 and that the area where the microorganisms did not exist was formed at the outer part of the test pieces placed on the agar.

EXAMPLE V

Preservation of fresh fish from decay:

A 1% aqueous solution of the test compound was prepared and added to sea water so as to make a predetermined concentration of the test compound. Horse mackerels were dipped in the sea water for about 30 minutes, dehydrated and preserved at 5° C in a refrigerator. A degree of freshness was decided by determining the amount of the volatile basic nitrogen contained in the fish according to the Kjeldahl's method.

The results are shown in Table 6.

Table 6

| Compound No. | Concentration of active ingredient in sea water (ppm) | Amount of volatile basic nitrogen (mg %) After 3 days | After 8 days | After 12 days |
|---|---|---|---|---|
| 1 | 5 | 10 | 17 | 28 |
| 2 | 5 | 11 | 20 | 30 |
| 6 | 5 | 10 | 18 | 29 |
| i | 5 | 15 | 36 | 71 |
| iii | 5 | 16 | 39 | 73 |
| Untreated plot | 0 | 18 | 46 | 80 |

EXAMPLE VI

Use in synthetic resin:

Sixtyfive parts of polyvinyl chloride powder, 35 parts of dibutyl sebacate, 2 parts of dibutyltin dilaurate and 0.5 part of the test compound (i.e. Compound No. 1 or 2) were mixed. The mixture was uniformly kneaded at 160° C for 10 minutes on a set of mixing rollers and extruded into a sheet of 0.3 mm in thickness. The sheet was cut into round test pieces of 20 mm in diameter, and the test pieces were treated in the same manner as in Example IV. Neither *Staphylococcus aureus* 209 P nor *Escherichia coli* K-12 was detected on the test pieces treated with each of Compound Nos. 1 and 2, and the area where the microorganisms did not exist was formed at the outer part of the test pieces placed on the agar.

EXAMPLE VII

Protective activity on white water:

Ten grams of each of the test compounds (i.e. Compound Nos. 1, 2, 3, 4, 5 and 6) were dissolved or suspended in 100 ml of water, and 5 ml of each solution was diluted with 1 liter of the white water resulting from a groundwood-pulp production process. Five milliliters of each resulting solution was further diluted with 2 liters of the white water. To 100 ml of the test solution thus obtained were added 10 g of grape sugar, 1 g of peptone, 0.05 g of magnesium sulfate and 0.01 g of calcium chloride, and the mixture was sterilized by heating and inoculated with *Bacillus* sp. isolated from the slime resulting from a paper-making process. Propagation of the fungus was not detected at all.

EXAMPLE VIII

Use in paint:

| Materials | Parts |
|---|---|
| Test compound | 10 |
| Zinc oxide | 20 |
| Red iron oxide | 10 |
| Precipitated barium sulfate | 10 |
| Linseed oil | 10 |
| Rosin | 20 |
| Naphtha | 20 |

Three grams of the paint prepared by the above-mentioned formulation were applied by brushing on a vinylchloride resin panel (30 cm × 20 cm × 5 mm) and dried. Each panel was attached to a wooden frame and dipped in the sea (the Toba Bay, Mie Prefecture, Japan) so that the lower half of the panel was under the sea surface (June 20th). After two months, the panel was taken out and the protective activity was checked and evaluated based on the proportion of the area to which marine life attached. The criteria for evaluation were as follows:

| Evaluation index | Proportion of the area |
|---|---|
| 0 | No life attached |
| 1 | Less than 2 % |
| 2 | 2 – 5 % |
| 3 | 5 – 20 % |
| 4 | 20 – 60 % |
| 5 | More than 60 % |

The results are shown in Table 7.

Table 7

| Compound No. | Marine life | | |
|---|---|---|---|
| | Slime | Sea lettuce | Barnacle |
| 1 | 0 | 0 | 0 |
| 2 | 0 | 1 | 1 |
| 3 | 0 | 1 | 1 |
| 4 | 1 | 2 | 2 |
| 5 | 1 | 2 | 2 |
| 6 | 1 | 1 | 2 |
| i | 3 | 4 | 4 |
| ii | 4 | 4 | 5 |
| iii | 3 | 4 | 4 |
| iv | 4 | 4 | 5 |
| Untreated plot | 5 | 5 | 5 |

EXAMPLE IX

Antimicrobial activity:

The test compound (i.e. Compound No. 5) was tested for its antimicrobial activity against filamentous fungi and bacteria according to the agar dilution method. As for the filamentous fungi (mold), a disc-inoculum of 5 mm in diameter was inoculated on a medium containing the test compound (potato agar medium) and incubated at 27° C for a required term. Thereafter, the state of growth of the fungi was checked. As for the bacteria, one loopful amount of the bacterial suspension was inoculated on a medium containing the test compound (heart infusion agar medium) and incubated at 37° C for 18 hours according to the Nippon Kagaku Ryoho Gakkai's method. Thereafter, the state of growth of the bacteria was checked.

The results are shown in Tables 8 and 9.

Table 8

| Test fungus | Incubation term (day) | Minimun inhibitory concentration (ppm) |
|---|---|---|
| Aspergillus niger | 4 | 100 |
| Penicillium citrinum | 4 | 200 |
| Rhizopus nigricans | 2 | 20 |
| Cladosporium herbarum | 4 | 100 |
| Chaetomium globosum | 3 | 10 |

Table 9

| Test bacterium | Minimum inhibitory concentration (ppm) |
|---|---|
| Sarcina lutea | 50 |
| Klebsiella pneumonia | 25 |
| Proteus mirabilis | 50 |
| Proteus vulgaris | 50 |
| Pseudomonas aeruginosa | 50 |
| Xanthomonas oryzae | 10 |

What is claimed is:

1. A method of controlling undesired vegetation which comprises applying to the locus thereof an effective amount of a herbicidal composition comprising a pyridyltriazinone compound of the formula:

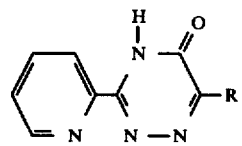

wherein R is a hydrogen atom, an alkyl group having 1 to 5 carbon atoms, an alkoxycarbonylmethyl group wherein the alkoxy has 1 to 3 carbon atoms or a phenyl group.

2. The method of claim 1, wherein the pyridyltriazinone compound is present as the active ingredient in said herbical composition in an amount of from 0.1 to 95% by weight.

3. The method according to claim 1, wherein the pyridyltriazinone compound has the formula:

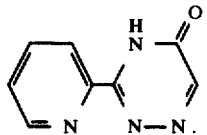

4. The method according to claim 1, wherein the pyridyltriazinone compound has the formula:

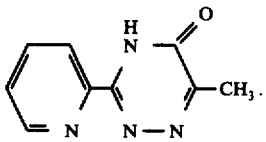

5. The method according to claim 1, wherein the pyridyltraizinone compound has the formula:

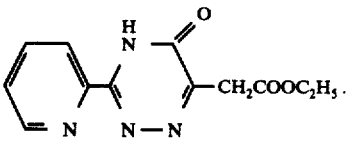

6. The method according to claim 1, wherein the composition is in the form of a dust, wettable powder, solution, granule, fine granule, emulsifiable concentrate, oil spray or aerosol.

* * * * *